(12) United States Patent
Amasino et al.

(10) Patent No.: US 7,303,918 B2
(45) Date of Patent: Dec. 4, 2007

(54) ALTERATION OF FLOWERING TIME IN PLANTS

(75) Inventors: Richard Mark Amasino, Madison, WI (US); Fritz Michael Schomburg, Madison, WI (US); Scott Daniel Michaels, Madison, WI (US); Si-Bum Sung, Madison, WI (US); Katia Scortecci, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 581 days.

(21) Appl. No.: 10/600,948

(22) Filed: Jun. 20, 2003

(65) Prior Publication Data

US 2005/0091717 A1 Apr. 28, 2005

Related U.S. Application Data

(62) Division of application No. 09/513,775, filed on Feb. 25, 2000, now Pat. No. 6,693,228.

(60) Provisional application No. 60/123,455, filed on Mar. 9, 1999, provisional application No. 60/121,572, filed on Feb. 25, 1999.

(51) Int. Cl.
*C12N 15/82* (2006.01)
*C12N 15/29* (2006.01)
*A01H 5/00* (2006.01)
*A01H 5/10* (2006.01)
*C12N 5/10* (2006.01)

(52) U.S. Cl. .................. 435/468; 536/23.6; 800/290; 800/298; 435/320.1

(58) Field of Classification Search ..................... None
See application file for complete search history.

*Primary Examiner*—Ashwin Mehta
(74) *Attorney, Agent, or Firm*—Quarles & Brady LLP

(57) ABSTRACT

The present invention provides genetic identification and use information about a family of genes, the FLOWERING LOCUS C (FLC) genes, that is part of the regulate the timing of the onset of flowering in plants. This information enables creation of transgenic plants in which the timing of the flowering of the plants has been selectively altered. Since these genes natively act to delay the time of flowering in plants, enhancing activity of the FLC protein delays the timing of flowering initiation while inhibiting the activity of FLC advances the timing of the start of flowering. A representative number of samples of the gene family are described. Members of the gene family are demonstrated to work in other plant species as well.

9 Claims, 2 Drawing Sheets

ALTERATION OF FLOWERING TIME IN PLANTS

CROSS-REFERENCE TO RELATED APPLICATIONS

Figure 1A:
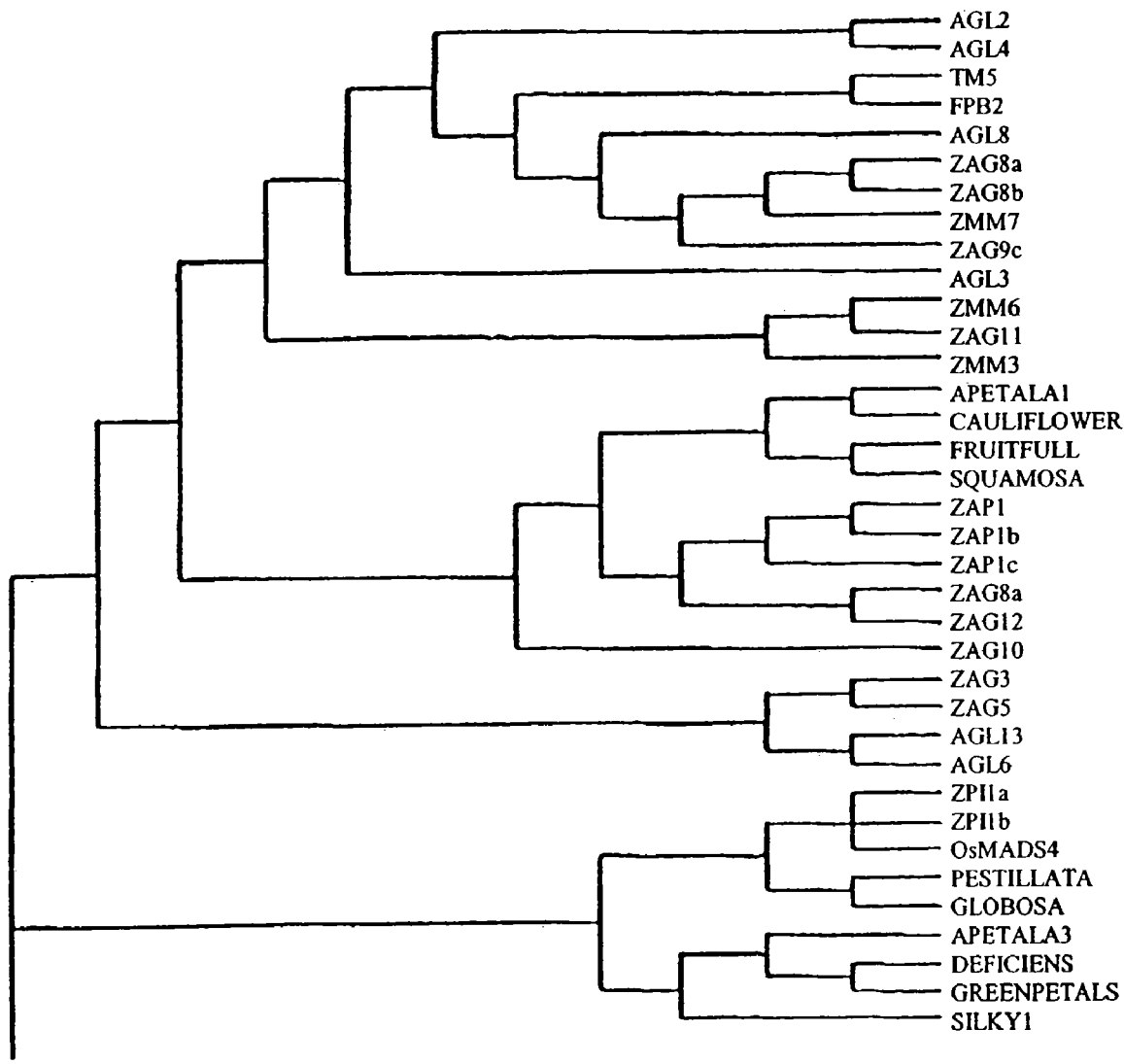

This application is a divisional of Application Ser. No. 09/513,775, filed Feb. 25, 2000, now U.S. Pat. No. 6,693,228, which claimed priority from provisional patent application Ser. No. 60/121,572 filed Feb. 25, 1999, and provisional patent application Ser. No. 60/123,455 filed Mar. 9, 1999.

STATEMENT REGARDING FEDERALLY SPONSORED RESEARCH OR DEVELOPMENT

This invention was made with United States government support awarded by the following agencies: USDA USDA/CSREES 95-37100-1614. The United States government has certain rights in this invention.

FIELD OF THE INVENTION

This invention relates to the control of the time of flowering in plants by genetic engineering. Specifically, this invention relates to the control of the timing of flowering by manipulation of the activity of the FLOWERING LOCUS C (FLC) family of genes.

BACKGROUND OF THE INVENTION

The transition of growing plantlets from vegetative growth to flowering is the major developmental switch in the plant life cycle. The timing of flower initiation is critical for the reproductive success of wild plants, and most plant species have evolved systems to precisely regulate flowering time. These systems monitor both environmental cues and the developmental state of the plant to control flowering.

Two commonly monitored environmental cues are photoperiod and temperature. In the photoperiod-responsive plants so examined, daylength is perceived in leaves and flowering signals appear to be translocated from leaves to meristems (Zeevaart, *Light and the Flowering Process*, Process, eds., D. Vince-Prue, B. Thomas and K. E. Cockshull, 137-142, Academic Press, Orlando, 1984.). Exposure to cold temperatures promotes flowering by a process known as vernalization. Vernalization affects meristems directly, perhaps by causing them to become competent to perceive flowering signals (Lang, *Encyclopedia of Plant Physiology*, ed., W. Ruhland, 15 (Part 1), 1371-1536, Springer-Verlag, Berlin, 1965). Other environmental cues that can affect flowering include light quality and nutritional status.

The developmental state of the plant can also influence flowering time. Most species go through a juvenile phase during which flowering is suppressed, and eventually undergo a transition to an adult phase in which the plant is competent to flower (Poethig, *Science*, 250, 923-930, 1990). This "phase change" permits the plant to reach a proper size for productive flowering.

In the flowering literature, the developmental flowering pathways are often referred to as autonomous to indicate that they do not involve the sensing of environmental variables. However, it is unlikely that autonomous and environmental pathways are entirely distinct. For example, day-neutral species of tobacco flower after producing a specific number of nodes and thus could be classified as flowering entirely through an autonomous pathway, but grafting studies indicate that day-neutral and photoperiod-responsive tobacco species respond to similar translocatable flowering signals (Lang et al., *Proc. Natl. Acad. Sci., USA*, 74, 2412-2416, 1977; McDaniel et al., *Plant J.*, 9, 55-61, 1996). Thus aspects of the underlying biochemistry of these pathways appear to be conserved.

Genetic analyses in several species has identified genes that affect the timing of flowering. The most extensive genetic analysis of flowering-time genes has been performed in *Arabidopsis thaliana*. In *Arabidopsis*, flowering-time genes have been identified by two approaches. One approach has been to induce mutations that affect flowering time in early-flowering varieties. Such mutations can cause either late-flowering or even earlier flowering. Late-flowering mutations identify genes whose wild-type role is to promote flowering and early-flowering mutations identify inhibitory ones. Studies in *Arabidopsis* have identified over 20 loci for which mutations specifically affect flowering time and several other loci that affect flowering time as well as other aspects of development (e.g., det2, cop1, ga1and phyB) (Koornneef et al., *Ann. Rev. Plant Physiol., Plant Mol. Biol.*, 49, 345-370, 1998; Weigel, *Ann. Rev. Genetics*, 29, 19-39, 1995).

Another approach to identify flowering-time genes is to determine the genetic basis of naturally occurring variation in flowering time. Although the varieties of *Arabidopsis* most commonly used in the laboratory are early-flowering, most varieties are late-flowering. Late-flowering varieties differ from early-flowering ones in that the late-flowering varieties contain dominant alelles at two loci, *FRIGIDA* (FRI) and *FLOWERING LOCUS C* (FLC) that suppress flowering (Sanda et al., *Plant Physiol.*, 111, 641-645, 1996; Lee et al., *Plant Journal*, 6, 903-909, 1994; Clarke et al., *Mol. Gen. Genet.*, 242, 81-89, 1994; Koornneef et al., *Plant Journal*, 6, 911-919, 1994).

Physiological analyses of flowering-time mutants and naturally occurring variation in flowering time indicate that flowering is controlled by multiple pathways in *Arabidopsis* (Koornneef et al., *Ann. Rev. Plant Physiol., Plant Mol. Biol.*, 49, 345-370, 1998). One group of late-flowering mutants (fca, fpa, fve, fy, ld) and plants containing the late-flowering FLC and FRI alleles are delayed in flowering in inductive (long-day) conditions and are even more severely delayed in short days. Vernalization of these late-flowering lines can suppress the late-flowering phenotype. Another group of late-flowering mutants (co, fd, fe, fha, ft, fwa, gi) exhibit a slight or no difference in flowering time when grown in short days compared to long days. Furthermore, this group shows little or no response to vernalization. Double mutants within a group do not flower significantly later than either single-mutant parent, whereas double mutants containing a mutation in each group flower later than the single-mutant parents (Koornneef et al., *Genetics*, 148, 885-92, 1998). Thus, there appears to be parallel flowering pathways that mediate the flowering response to environmental and developmental cues. A photoperiod pathway promotes flowering in long days. A pathway referred to in the literature as autonomous (because the photoperiod response is not affected by mutations in this pathway) appears to control the age, or more specifically the developmental stage, at which plants are competent to flower. Recent support of the developmental role of this pathway is the demonstration that autonomous pathway mutants exhibit changes such as alterations of trichome patterns that indicate such mutant plants are delayed in the juvenile to adult transition (Telfer et al., *Development*, 124, 645-654, 1997).

Blocks to the autonomous pathway due to mutant fca, fpa, fve, fy, and ld alleles or to the presence of dominant late-flowering FLC and FRI alleles can be bypassed by vernalization (Koornneef et al., Ann. Rev. Plant Physiol., Plant Mol. Biol., 49, 345-370, 1998). Thus FLC and FRI can be regarded as genes that create a requirement for vernalization. Other species, particularly *Brassicas*, appear to have the same "circuitry" as *Arabidopsis*. This similarity has been most thoroughly analyzed for the relationship between dominant suppressors of flowering and vernalization in *Brassicas*. The major difference between annual and biennial cultivars of oilseed *Brassica napus* and *B. rapa* is conferred by genes controlling vernalization-responsive flowering time (Osborn et al., Genetics Society of America, 146, 1123-1129, 1997). By comparing quantitative trait loci (QTLs) in segregating populations of annual X biennial varieties of *B. rapa* and *B. napus*, it was shown that the 2 major QTLs that confer vernalization-responsive late flowering in *B. napus* and *B. rapa* are likely to be the same (Osborn et al., Genetics Society of America, 146, 1123-1129, 1997). In *B. rapa* the two flowering-time QTLs were separated in recombinant inbred populations and the QTL with the greatest effect on flowering time was VFR2 (vernalization-responsive flowering time in rapa 2). Furthermore, VFR2 appears to correspond to FLC from *Arabidopsis*: VFR2 was mapped at high resolution using hybridization probes that permit a comparison of *Arabidopsis* and *Brassicas* after introgression of the late allele into the early-flowering annual variety, and only a probe corresponding to FLC detected no recombination events with VFR2 (<0.44 cm) indicating that VFR2 is an FLC homolog.

The timing of flowering is of great importance in agriculture and horticulture. In horticultural crops the product is often the flowers. In food, feed crops, or fiber crops, such as the cereals rice, wheat, maize, barley, and oats, and dicots such as soybeans, canola, and cotton, sunflower, tomato, broccoli, and other members of the legume family, the product is often flowers or the result of flowering—fruits, seeds, or seedpods. Understanding the molecular basics of flowering-time control will lead to strategies to optimize flower, fruit, and seed production by genetic manipulations that modify the timing of flowering. For example, in certain crops accelerating the onset of flowering would permit that crop to be grown in a region where the growing season is otherwise too short, or permit multiple crops in a region where only one crop is currently possible.

There are also crops in which the non-flowering parts of the plant are the useful part. In such crops preventing or substantially delaying flowering will increase the yield of these useful parts. Examples of plants in which delaying or preventing flowering would be desirable include forage crops such as alfalfa and clover, vegetables such as cabbage and related *Brassicas*, spinach, and lettuce. In crops in which underground parts are used, such as sugar beet or potato, delaying or preventing flowering should increase yield. Also, in sugar beet, prevention of flowering will permit more energy to be devoted to sugar production. Likewise the yield of wood and biomass crops will be increased by delaying flowering. Thus, there is a need and significant advantage to understanding the molecular basics of flowering-time control.

SUMMARY OF THE INVENTION

The present invention encompasses a gene family for the *FLOWERING LOCUS C* (FLC) genes that are one of the significant controlling factors in the repression of flowering. The invention includes the DNA sequences for these genes as well as the expressed polypeptides and proteins from these genes.

The present invention is also directed at transgenic plants which have altered flowering characteristics from non-transgenic plants of the same species due to the presence of a transgene which affects the level or timing of FLC protein activity in the transgenic plants.

It is an object of the present invention to provide a tool to creators of new plant varieties to be able to alter the timing of flowering in the plant species. The timing of flowering can be made earlier or later, depending on the desires of the plant breeder, by changes to the levels of the FLC genes in the plants.

This permits plants to be modified in a very useful way. Since flowering is an important physiological stage for a flowering plant, the ability to manipulate flowering time in a plant species makes it possible either to increase vegetative growth or flower creation by a plant, whichever is more desired in the instance.

Other objects advantages and features of the present invention will become apparent from the following specification and the attached drawing figures.

BRIEF DESCRIPTION OF THE DRAWING FIGURE

Figure 1B:
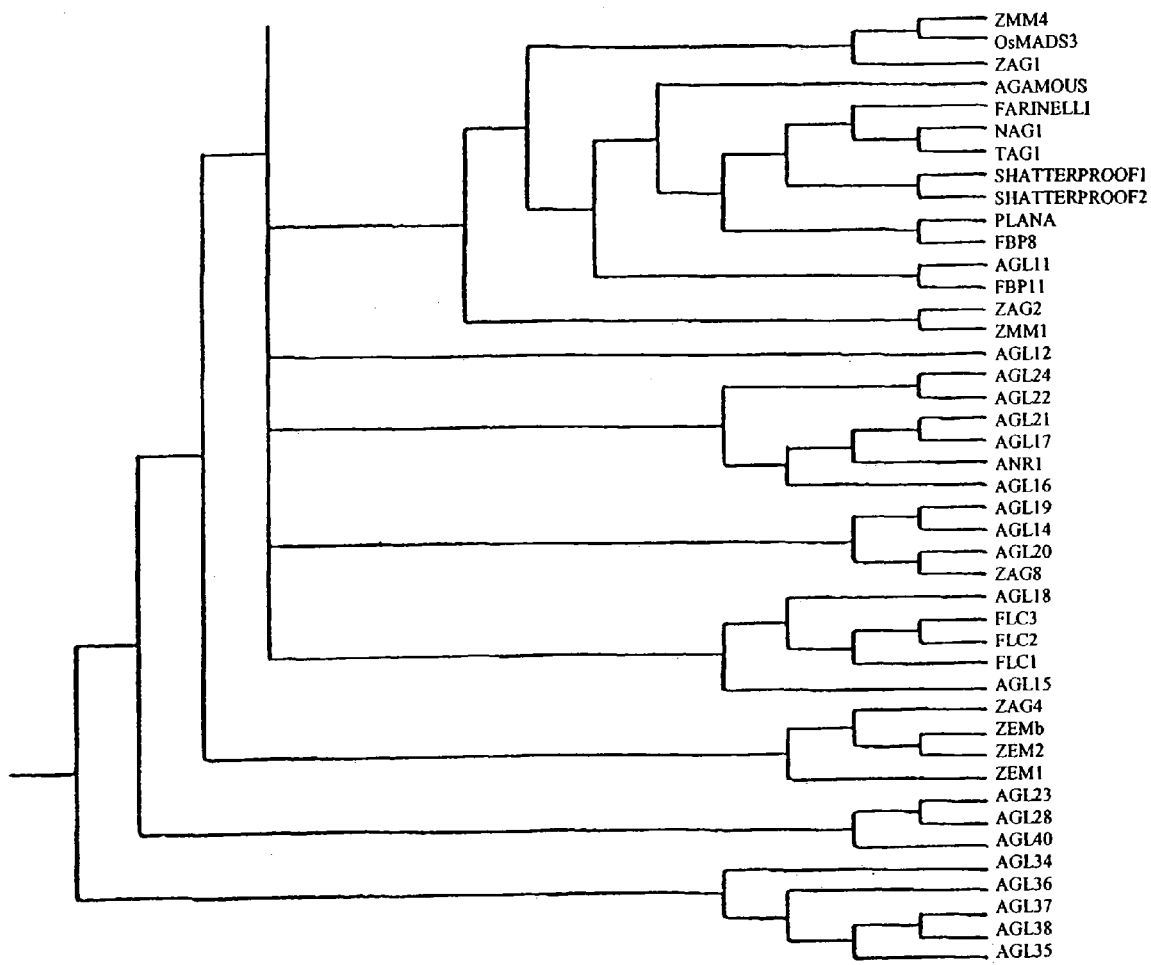

FIG. 1 is a phylogenic diagram of the relative degree of relatedness among members of the MADS box class of plant genes.

DETAILED DESCRIPTION OF THE INVENTION

This disclosure is directed at the nucleotide and protein sequences for the genes of the *FLOWERING LOCUS C* (FLC) family of plant genes. As described below, it turns out that plants commonly have more than one FLC gene in their genome. The FLC genes are, however, similar and homologous. It is disclosed here that these genes can be used to make transgenic plants that have altered flowering characteristics. With the knowledge about the FLC genes described here, it becomes possible to both advance flowering time in a transgenic plant, by repressing FLC activity, or to retard flowering time in a plant, by increasing FLC activity in a plant. This thus gives plant breeders and creators a unique tool so as to sculpt the flowering time characteristics of a crop plant to more closely follow the desires of the breeder.

Set forth below is the nucleotide and amino acid sequences for several FLC genes. The work that gave rise to this document began with the isolation and sequencing of a gene from *Arabidopsis thaliana*, here named FLC1. Using that information and other genetic information, some of which is discussed below, several other FLC genes were discovered. It turns out that *Arabidopsis*, which is extensively studied in plant genetic laboratories since it has one of the smallest genomes of all plants, has at least three FLC genes, here designated FLC1 (SEQ ID NO: 1), FLC2 (SEQ ID NO: 3) and FLC3 (SEQ ID NO:5). Using the information from the three FLC gene found in *Arabidopsis*, two FLC genes from *Brassica* (SEQ ID NO: 7 and 9) have been identified so far. These genes have several characteristics which will be shared by all other plant FLC genes.

The FLC genes are part of a category of genes referred to as MADS box genes. The MADS box is a highly conserve motif shared by a group of evolutionarily related transcription factors. The name MADS is an acronym for the original genes first identified as sharing the common MADS box domain. There are a large number of MADS box genes which have been identified so far, and there is ongoing work to further organize these genes into sub-groups. In plants, the MADS box genes are known to affect many aspects of plant development, including structural development. Two of the FLC genes identified here, (*Arabidopsis* FLC2 and FLC3) have been previously sequenced as a part of the *Arabidopsis* genome sequencing effort, although their function was not previously known.

FIG. 1, which uses data originally accumulated by Martin Yanofsky and Elena Alvarez-Buylla, UC San Diego, is a phylogenic tree illustration of the relative degree of relationship among MADS-box proteins so far identified from *Arabidopsis* and maize. Note that the three identified FLC genes are all more closely related to each other than they are related to any other MADS box genes.

Set forth below in the sequence listing is the cDNA sequence, and the deduced amino acid sequence, for each of FLC1 (SEQ ID NO: 1 and 2), FLC2 (SEQ ID NO: 3 and 4) and FLC3 (SEQ ID NO: 5 and 6) from *Arabidopsis thaliana*, as well as BrFLC1A (SEQ ID NO: 7 and 8) and BrFLC1B (SEQ ID NO: 9 and 10) from *Brassica rapa*. Also presented below is some sequence comparison data. This data indicates that the FLC1 and FLC2 genes from *Arabidopsis* are 60% identical over their entire length, and still over 50% identical over their entire region outside of the MADS box region. The latter comparison may be more important since all of the MADS box genes have a relatively high degree of conservation in the MADS box region itself. For the purposes of this analysis, the MADS box region is considered to be the first 60 amino acids at the amino terminus of the protein sequences. This degree of sequence similarity appears to hold across species. The Brassica genes BrFLC1a and BrFLC1B are actually more identical to FLC1 than FLC1 is to FLC2. The identity of FLC2 to the *Brassica* genes is slightly less than 50% outside of the MADS box, so among the variants in the FLC gene family, identity at the amino acid levels is likely to generally be above 40%. Thus, amino acid identity of over 40% outside the MADS box regions is one indication of a member of the FLC gene family.

Note again the phylogenic chart of FIG. 1. It is significant that the three identified FLC genes from *Arabidopsis* are all more closely related to each other than to any other *Arabidopsis* MADS box genes. Since it is believed that the full spectrum of MADS box genes used by the plant is known, (at least in *Arabidopsis* from the nearly complete genome sequencing effort), one can chart out, using commonly available sequence analysis and matching software, the relatedness of any newly sequenced gene to the members of the MADS box family of genes as shown on FIG. 1. A member of the FLC gene family is a gene which maps by phylogenic analysis to be closer to *Arabidopsis* FLC1, FLC2 or FLC3, by phylogenic sequence analysis, than to any other MADS box gene from *Arabidopsis*.

A way of confirming that a gene is a member of the FLC gene family is by testing the gene for effect on the timing of plant flowering. Described in the examples below are tests to demonstrate that the FLC genes do, in fact, act to delay flowering in transgenic plants. By testing a possible FLC gene for similar effect in transgenic plants, using *Arabidopsis* as a model, the activity of a putative FLC gene from another plant species can be confirmed.

It should be emphasized that what this tool enables is the alteration of the flowering time of a plant. The normal function of FLC is to delay or inhibit flowering. However, the availability of the genetic sequences of the FLC genes enable the time of flowering in a plant to be altered in either direction. Several techniques are now known to be practical to either down-regulate or up-regulate the expression of an endogenous plant gene. To down-regulate gene expression, an antisense version of the coding sequence of the gene can be inserted into the plant, or the level of gene expression can be lowered by co-suppression, a poorly understood phenomenon by which insertion of an artificial gene construct into a plant occasionally causes suppression of both the inserted gene and any other genes homologous to it. To up-regulate a plant gene, extra copies of the gene can be introduced into the plant, preferably by germ line transformation of the plant genome, and by properly choosing the strength and characteristics of the plant promoter chosen, the level of activity of the protein produced by the native gene can be increased in the cells and tissues of the plant.

It should be understood that techniques of plant genetic engineering have been developed to the point where it is now practical to place any genetic construct into almost any useful plant species. The process does, however, still involve some random processes, most notably that insertions of foreign DNA into the genome of plants still occurs at random sites in the plant genome. As a result, in any group of plants emerging from a plant transformation process, the results achieved for the different gene insertion events will vary, sometimes dramatically. For example, for a simple gene insertion of another copy of an endogenous plant gene, many plants produced will have a slightly higher level of activity of the endogenous protein, others will have no measurable change or even a decrease in measurable activity, while a few will have substantial increases in activity levels. However, this variation does not mean stable results cannot be achieved, since the results tend to be consistent generation-to-generation for each specific genetic insertion. Thus the high activity plants have, in effect, a high activity allele that can be transferred by normal mendelian inheritance to their progeny.

To make a transgenic plant, as is known to those of skill in the art, one needs to make a genetic construction capable of expressing an inserted protein coding sequence, whether foreign or endogenous, in a plant. One also needs a method to insert the genetic construction into the plant.

The tools and techniques for making genetic constructions that will express proteins in plants are now widely known. Any genetic construction intended to cause the synthesis in the cells of the plant of a polypeptide or protein must include a sequence of DNA known as a protein coding sequence, which specifies the sequence of the polypeptide or protein to be produced in the resultant plant. For a protein coding sequence to be expressed in a plant to produce a polypeptide or protein, it must be placed under the control of a plant expressible promoter and be followed by a plant transcriptional terminator sequence, also known as a polyadenlyation sequence. The plant expressible promoter is a promoter which will work in plants, usually either of plant origin or from a plant pathogen like a virus (e.g. Cauliflower mosaic virus) or a bacteria (e.g. *Agrobacterium* promoters like the nopaline synthase promoter). Plant promoters from pathogens tend to be constitutive promoters, meaning that they actually express the protein coding sequence in all of the tissues of the plant at all times. Other plant promoters are known to be tissue specific (e.g. to fruit or to flower) or developmentally specific (e.g. to stage of plant life such as emergent specific or senescent specific), while others are intended to be inducible (e.g. heat shock or metal ion induced promoters). Any of these types of promoters may by used in the practice of this invention depending on the intended affect on the transgenic plant to be produced.

Not all genetic constructions are intended to produce a polypeptide or protein in the cells of the transgenic plant. If the object of the manipulation is to lower the activity level of the target protein in the plant, the genetic construction can be one intended to lower endogenous levels of protein activity without producing a protein in the plant. One well-known method to accomplish this is through the use of antisense technology, in which a genetic construct is created which causes the synthesis in the cells of the plant of an mRNA strand complementary to some portion of the mRNA created during the expression of the target gene. The antisense RNA interferes with the translation of the target mRNA and less protein is produced in the affected plant cells.

Several methods have been demonstrated to insert genes into plants to make them transgenic. The most widely used methods, broadly defined, are *Agrobacterium*-mediated transformation or accelerated particle mediated transformation. The various techniques of *Agrobacterium*-mediated plant transformation make use of the natural ability of the plant pathogens of the *Agrobacterium* genus to transfer DNA from a plasmid in the bacteria into the genome of a plant cell. Particle-mediated plant transformation techniques utilize DNA-coated small carrier particles accelerated from a device, often referred to as a gene gun, into the cells of a plant. The full implementation of either approach requires techniques to recover a fully mature, morphologically normal plant from the transformed cells. The techniques often therefore involve either selection or screening protocols to identify which plant cells were transformed and regeneration protocols to recover whole plants from the single transformed plants cells. As mentioned above, these techniques have been worked out for many plant species and many, and perhaps all, of the economically important plant species. Other techniques, such as electroporation have also been used to make transgenic plants. But fundamentally for the invention disclosed here, the particular technique of plant transformation does not matter. Once the plant has been genetically engineered, and a transgenic plant has been created, the method of transformation of the original plant becomes irrelevant. A transgene inserted into the genome of one plant is then fully inheritable by progeny plants of the original genetically engineered plant by normal rules of classical plant breeding. The term transgene is here used to apply to an inserted genetic construction carried in the cells of a target plant. Thus, the term transgenic plant, as used here, refers to a plant that carries such a transgene.

Disclosed here is information about a set of plant genes, the FLC genes. While these genes have existed previously in their native, or altered, state in plants, this disclosure is believed to be the first disclosure of these genes in isolated form. By isolated form, it is meant that the genes have been isolated from their host plants. Now the information from those genes becomes available for use in in vitro manipulations of the genes and their components to create genetic constructions for several uses. One contemplated use is the creation of transgenic plants. Another contemplated use is the diagnosis and analysis of plants, both transgenic and non-transgenic, to analyze and determine their pattern of FLC gene activity as an aid to breeding or creating plants having desired flowering time characteristics.

For example, as set forth in further detail below, plants that lack FLC activity, as a result of mutations in FLC, flower much earlier than those containing an active FLC allele. Plants with wild type FLC activity had about 6 times the number of leaves as the plants with decreased FLC activity. Furthermore, plants genetically engineered to express FLC at higher than normal levels exhibit substantially delayed flowering. While the examples set forth below are executed in *Arabidopsis*, due to the simplicity in the genetic manipulation of that plant, the same techniques will work in other plants species. In fact, the high degree of sequence identity among the FLC genes indicates that the members of the FLC gene family from one plant species will function, as a general rule, even in other plants species.

The flower time regulation FLC gene is a repressor of flower initiation in plants. It is believed that the flower initiation polynucleotide fragment of FLC plays a central role in flower initiation control because other genes that regulate flowering act by modulating the activity of this gene. This gene is, however, not the sole factor in determing flowering time in a plant. For example, it has been shown that the locus denominated FRIGIDA (FRI) is a co-repressor of flowering that acts synergistically with FLC (Lee et al., Plant Journal, 6, 903-909, 1994.). Conversely the gene LUMINIDEPENDENS, which acts to promote flowering, does so by decreasing FLC levels. In mutants that lack LUMINIDEPENDENS activity, which are delayed in flowering, FLC levels are substantially increased. Thus, modulating a flower initiation regulator is a reliable means to control the time of flower initiation.

It has further been discovered that FRI acts to increase FLC levels. In fact, the two genes FLC and FRI are two dominant alleles which interact to cause late flowering. Using conventional nomenclature, lower case (e.g. fri, flc) refers a recessive, or inactive allele, and upper case (e.g. FRI, FLC) refers to the active dominant allele. Both dominant alleles are normally required to achieve late flowering. Thus plants which will be early flowering include the genetic combinations: fri/fri and flc1/flc1; fri/fri and FLC1/flc1; fri/fri and FLC1/FLC1; FRI/fri and flc1/flc1; and FRI/FRI and flc1/flc1. Genetic combinations which will be late flowering will be: FRI/fri/ and FLC1/flc1: FRI/FRI and FLC1/flc1; FRI/fri and FLC1FLC1; and FIR/FRI and FLC1/FLC1. Thus in testing non-transgenic lines for mutant forms of FLC1, it is convenient to cross the plant containing an FLC1 allele of unknown activity to a tester line containing, and preferable homozygous for, the FRI allele so as to reveal (or not) the presence of an active FLC1 allele.

The lifetime of a plant can be divided into at least two phases, the vegetative phase and the reproductive phase. In most commercially important crop plants, during the vegetative phase the plant continues growth, which includes increasing in size and in the number of leaves present on the plant. The reproductive phase begins with flower initiation. At that point much of the plant's further growth is the growth (or development) of flowers, fruits, and seeds. Commercially important crop plants have been bred for desirable characteristics, including uniformity in the time the plants are ready for harvesting. This has resulted in a high degree of uniformity in the number of leaves present on each plant in a population of plants grown under the same conditions. Due to the uniformity in the number of leaves present, alterations in the time of flower initiation can often be measured as a function of the number of leaves on a plant. For instance, if flower initiation is activated early in a plant, that plant will have fewer leaves relative to the same plant grown under the same conditions that do not activate flower initiation early. Moreover, a plant that activates flower initiation early can also be said to have a shortened vegetative phase relative to the same plant grown under the same conditions that do not activate flower initiation early. Likewise, if flower initiation is repressed such that the plant undergoes flower initiation later, that plant will have more leaves relative to the same plant grown under the same conditions that do not repress flower initiation until later. Moreover, a plant that represses flower initiation may also be said to have a prolonged vegetative phase relative to the same plant grown under the same conditions that do not repress flower initiation. Alterations in the time of flower initiation can also be measured as a function of time.

Plants in which a copy of an FLC gene is introduced may also contain a wild-type (i.e., endogenous) flower time regulation coding region which acts to repress flower initiation. Upon introduction into the genome of a plant, the FLC gene can act to augment the activity of an endogenous flower time regulation coding region to make flower initiation occur later. For instance, a second copy of a flower time regulation coding region can be introduced into a plant to increase the amount of flower time regulation FLC protein present in the plant. Expression of a portion of an FLC protein encoded by a portion of the flower time regulation coding region can also lead to activation of flowering in a plant. A portion of a polypeptide which leads to activation of flowering in a plant can be referred to as a dominant negative mutant, and is further described herein.

The present invention also provides a genetically modified plant, characterized as having the phenotypic trait of altered time of flower initiation. By this it is meant that the modified plants of the present invention, whether modified by incorporating an FLC gene expressing a new or additional FLC protein in the plant, or by inhibiting activity of an endogenous FLC gene in the plant, demonstrate a different length of time to the onset of flower initiation relative to the same plant without the transgene inserted. Preferably, flowering initiation (on average) in the transgenic plant occurs at least about 3 days, more preferably at least about 7 days, most preferably at least about 12 days after initiation of flowering in the same plant without the transgene. Alternatively, flowering initiation (on average) in the transgenic plant occurs at least about 3 days, more preferably at least about 7 days, most preferably at least about 12 days before initiation of flowering in the same plant without the transgene. Preferably, the genetically modified plant and the same plant without the transgene are grown under the same conditions. The actual data from Arabidopsis plants, as set forth below, demonstrates that even much more dramatic changes in plant flowering time are possible, from three weeks to three months or the reverse.

The different length of time to the onset of the flowering stage of the plant relative to the same plant without the transgene can also be measured by determining the difference in the number of leaves on the genetically modified plant at the time of flower initiation and the number of leaves on the same plant without the transgene at the time of flower initiation. Preferably, the transgenic plant exhibits at least about 10% more, more preferably at least about 50% more, most preferably at least about 80% more leaves at flower initiation than the same plant without the transgene. Alternatively, the transgenic plant exhibits at least about 10% fewer, more preferably at least about 50% fewer, most preferably at least about 80% fewer leaves at flower initiation than the same plant without the transgene. Preferably, the genetically modified plant and the same plant without the transgene are grown under the same conditions.

In one embodiment of the present invention, a nucleic acid molecule is provided that includes a polynucleotide having a nucleotide sequence that represents the coding region of the gene, FLOWERING LOCUS C (FLC), from *Arabidopsis thaliana*, or a portion thereof, as well as allelic variants in sequence of the FLC gene and homologs of the coding region of the FLC gene derived from other species. Homology is a relatedness that can be determined by, but not limited to, nucleic acid hybridization techniques, computer searches of databases, computer or manual comparisons of amino acid and nucleotide sequences, and protein detection with the use of FLC-specific antibodies. Two nucleotide sequences are "similar" if they can be aligned so that a percentage of corresponding residues are identical. Preferably, two nucleotide sequences have greater than about 31%, more preferably at least about 50%, even more preferably at least about 70%, and most preferably at least about 80% identity.

Accordingly, the invention includes genes and proteins which are members of the FLC family of plant genes and share a significant level of primary structure with the sequence of FLC1 presented below. The two amino acid sequences (i.e., the amino acid sequence of the homolog and the sequence of FLC1) are aligned such that the residues that make up the MADS domain, i.e., amino acids 1-60, are aligned in that region and then the entire length of the two amino acid sequences are further aligned to maximize the number of amino acids that they have in common along the lengths of their sequences. Gaps in either or both sequences are permitted in making the alignment in order to place the residues of the MADS domain in register and to maximize the number of shared amino acids, although the amino acids in each sequence must nonetheless remain in their proper order. The percentage amino acid identity is the higher of the following two numbers: (a) the number of amino acids that the two sequences have in common within the alignment, divided by the number of amino acids in FLC1, multiplied by 100; or (b) the number of amino acids that the two sequences have in common within the alignment, divided by the number of amino acids in the candidate polypeptide, multiplied by 100. Preferably, a flower time regulation polypeptide has greater than 40% identity, more preferably at least about 50% identity, most preferably at least about 70% identity, over the entire length of the FLC1 protein.

Sequence homology or identity is less important at the nucleotide level. As is well understood by those in the art, the degeneracy of the genetic code permits many DNA protein coding sequences to code for the same amino acid sequence. It is even possible, and common, to alter the coding sequences of native protein coding sequences as a part of making plant expression cassettes, without altering the amino acids sequence of the resultant proteins, for various cloning convenience reasons or for reasons of codon usage or preference in the target plant.

Isolated nucleic acid molecules of the invention can be obtained by several methods. For example, they can be isolated using procedures which are well known in the art. These include, but are not limited to: 1) hybridization of detectably labeled probes representing all or part of any one of the FLC genes to genomic or cDNA libraries to detect similar nucleic acid sequences; 2) antibody screening of expression libraries to detect similar structural features; 3) synthesis by the polymerase chain reaction (PCR); and 4)

chemical synthesis of a nucleic acid molecule. Sequences for specific coding regions of genes can also be found in GenBank, the National Institutes of Health computer database. The coding region can then be isolated and ligated into a vector as described below.

For the identification of isolated nucleic acid molecules using detectably labeled probes, or for the identification of polynucleotide fragments whose complements hybridize to FLC1, standard strigency hybridizing conditions are a modification of the conditions used by Church et al., Proc. Natl. Acad. Sci. USA, 81, 1991 1984: incubation in a solution containing 0.5 M phosphate buffer, pH 7.2, 7% sodium dodecyl sulfate (SDS), 10 mM EDTA, at 45° C. for 12 hours, and three 20-minute washes at 45° C. in a solution containing 2×SSC (1×SSC: 150 mM NaCl/15 mM sodium citrate, pH 7.0) and 0.1% SDS. Preferably, a polynucleotide (e.g., a probe) will hybridize to the nucleotide sequence set forth in SEQ ID NO:1 under standard stringency hybridizing conditions. Generally the polynucleotide (e.g., probe) does not have to be complementary to all the nucleotides of the polynucleotide fragment as long as there is hybridization under the above-stated conditions. Alternatively, higher stringency conditions can be used, for example by increasing the temperature of the hybridization and wash steps to 65° C., 60° C., 55° C., or 50° C. Moreover, the length of time required for hybridization can vary from 12 hours stated above. Typically, lower stringency hybridization conditions permit hybridization of related but not identical FLC genes, and thereby allow identification of FLC genes in other species. Preferably, hybridization and washing temperatures are, in increasing order of preference, at 68° C. hybridization and 65° C. wash, 60° C. hybridization and wash, 55° C. hybridization and wash, 50° C. hybridization and wash, most preferably 45° C. hybridization and wash.

Plants included in the invention are any flowering plants amenable to transformation techniques, including both monocotyledonous and dicotyledonous plants. Examples of monocotyledonous plants include, but are not limited to, vegetables such as asparagus, onions and garlic; cereals such as maize, barley, wheat, rice, sorghum, pearl millet, rye and oats; and grasses such as forage grasses and turfgrasses. Examples of dicotyledonous plants include, but are not limited to, vegetables, feed, and oil crops such as tomato, beans, soybeans, peppers, lettuce, peas, alfalfa, clover, *Brassica* species (e.g., cabbage, broccoli, cauliflower, brussel sprouts, rapeseed, and radish), carrot, beets, eggplant, spinach, cucumber, squash, melons, cantaloupe, sunflowers; fiber crops such as cotton; and various ornamentals such as flowers and shrubs.

While the examples described below demonstrate that increased expression of FLC delays or prevents flowering and loss of FLC function causes accelerated flowering, there are other obvious ways to modify FLC expression such that flowering time would be modified. For example, transgenes encoding dominant-negative versions of a flower time regulation polypeptide could be introduced into the plant genome. Dominant-negative mutants are proteins that actively interfere with the function of a normal, endogenous protein. Thus, the action of a gene can be blocked without inactivating the structural gene itself or its RNA. This strategy has been successful for transcription factors in the same MADS domain family as FLC. (Gauthier-Rouviere et al., *Exp Cell Res*, 209, 208-215, 1993; Mizukami et al., *Plant Cell*, 8, 831-845, 1996). In these experiments making dominant negatives using MADS-box genes, the most effective constructs were those that lack the C-terminal domain of the polypeptide. Since FLC, as with most MADS-box genes, share the same basic organization, a similar C-terminal truncation would be effective with FLC. This truncation would contain amino acids 1-150 of the full FLC1 protein, which corresponds to nucleotides 1-450 of the FLC1 gene.

The above disclosure generally describes the present invention. A more complete understanding can be obtained by reference to the following specific examples which are provided herein for purposes of illustration only and are not intended to limit the scope of the invention.

EXAMPLES

Example 1

Loss of FLC Function Causes Early Flowering

Naturally occurring late flowering in *Arabidopsis* is caused primarily by the interaction of two dominant genes, FLC1 (Lee, et al. *Plant Journal* 6, 903-909 1994; Koornneef, et al. *Plant Journal* 6, 911-919 1994) and *FRIGIDA* (FRI) (Lee, et al. *Mol Gen Genet* 237, 171-176 1993; Clarke and Dean. *Mol Gen Genet* 242, 81-89 1994). We further demonstrated that the late-flowering phenotype of FRI is suppressed in the Landsberg erecta (Ler)strain of *Arabidopsis* by a recessive allele of the FLC1 gene (Lee, et al. *Plant Journal* 6, 903-909 1994; Koornneef, et al. *Plant Journal* 6, 911-919 1994). Similarly, late flowering caused by mutations in the gene *LUMINIDEPENDENS* (LD) are also suppressed in the Ler background by the Ler allele of FLC1 (Lee, et al. *Plant Journal* 6, 903-909 1994; Koornneef, et al. *Plant Journal* 6, 911-919 1994). To determine if the ability of the Ler allele of FLC1 to suppress the late-flowering phenotype of both FRI and mutations in ld might be explained by a loss of function mutation in FLC1, mutagenized populations of *Arabidopsis* were created to screen for plants containing flc1 mutations. In one mutagenesis, 5,000 late-flowering ld mutant plants (ld-3) were mutagenized with ethylmethanesulfonate. From 50,000 M2 plants screened from this population one early-flowering plant was isolated that in complementation tests proved to be allelic to the recessive allele of FLC1 found in the Ler background. A second screen was carried out using a late-flowering line homozygous for the late-flowering FRI allele in the Columbia (Col) background. 90,000 seeds were treated with 5-6 krad of fast-neutron radiation. 300,000 M2 plants were screened for early flowering and 4 new flc1 alleles were isolated.

The lesions in 4 of induced flc1 alleles were determined. Data on the early-flowering phenotype of three fast-neutron flc1 alleles is presented in Tables 1 and 2. All 4 of the flc1 alleles contained mutations predicted to cause a total loss of function. In summary, loss of FLC1 gene function results in a total suppression of the late-flowering effect of FRI in both long days and short days. In an early-flowering non-FRI-containing background the loss of FLC1 gene function only effects flowering time under short day conditions. Thus the wild-type or active FLC1 clearly acts as an inhibitor of flowering.

TABLE 1

Effect of a loss-of-function flc1 mutations in an late-flowering, FRI-containing background

| Lines | Rosette leaf number at flowering |
|---|---|
| Long days-FRI-containing wild type | 74 (12)* |
| Long days-flc1-2 | 11.8 (.75) |
| Long days-flc1-3 | 12.0 (0.6) |
| Long days-flc1-4 | 11.8 (0.4) |
| Short days-FRI-containing wild type | >100 |
| Short days-flc1-3 | 44 (2.7) |

*Numbers in parentheses represent one standard deviation. The number of leaves formed before flowering is measure of flowering time. Thus, in a FRI containing background flc1 mutant plants consistently flower in $\frac{1}{6}^{th}$ the time of FLC1 containing, wild-type plants.

TABLE 2

Effect of a loss-of-function flc1 mutation in an early-flowering, non-FRI-containing background

| Lines | Rosette leaf number at flowering |
|---|---|
| Long days-Col wild type | 13.7 (0.8)* |
| Long days-flc1-3 | 13.2 (0.7) |
| Short days-Col wild type | 55.4 (4.7) |
| Short days-flc1-3 | 42.4 (3.5) |

*Numbers in parentheses represent one standard deviation. The number of leaves formed before flowering is measure of flowering time.

The lines described here were obtained from the *Arabidopsis* Biological Resource Center, Columbus, Ohio. Unless otherwise noted, the growth conditions were those generally known and used by a person of skill in the art. Due to the effect of vernalization on flower initiation, growth conditions did not include prolonged exposure of plants to cold temperatures (e.g., 0° C. to 8° C.). The techniques used to genetically analyze *Arabidopsis thaliana* are know to a person of skill in the art (see, e.g., Koornneef et al., Genetic Analysis, In: "*Arabidopsis* Protocols," Methods in Molecular Biology Series, vol. 8, Martinez-Zapater et al., (eds.), Humana Press, Totowa, N.J., pp. 105-227, 1998).

Example 2

Isolation of FLC by Positional Cloning

To generate a segregating population useful for high resolution mapping and positional cloning of FLC1, the $F_1$ plants generated from a cross of Ler (fri/fri,flc1/flc1) to Col (fri/fri;FLC1/FLC1) were crossed to the tester line containing the FRI in Ler(FRI/FRI,flc1/flc1). This tester line contained a late-flowering allele of FRI, but also contains the flc1-Ler allele and is, therefore, early flowering. The progeny of the cross of the $F_1$ to FRI in Ler, which segregated 1:1 for late and early flowering, were late flowering when FLC1-Col is present (i.e. FRI/fri;FLC1/flc1) due to the interaction between FRI and FLC1, but early flowering in the presence of flc1-Ler (i.e. FRI/fri;flc1/flc1). Test-cross progeny (4500 plants) were screened with the microsatellite markers nga158 and nga151 (Bell and Ecker, 1994), which had previously been shown to flank FLC1 (Lee et al., 1994b). Plants containing recombination events between nga158 and 151 were then tested with a third microsatellite marker nga249, which revealed that FLC1 resided in the interval between nga249 and nga151.

The region between nga249 and nga151 was contained within four yeast artificial chromosome (YAC) clones. To generate additional markers, we determined the DNA sequence of YAC end clones, and designed primers to amplify the corresponding sequences from Ler and Col. These DNAs from Ler and Col were sequenced to identify single-nucleotide changes, which were then used to create derived cleaved amplified polymorphic sequence (dCAPS) markers (Michaels and Amasino, 1998; Neff et al., 1998). Markers derived from the left and right ends of YAC CIC1B8 detected recombination events on either side of FLC1, demonstrating that FLC1 resided in the 620 kb interval spanned by CIC1B8.

A group of 13 BAC, TAC, and P1 clones have been identified by the Kazusa *Arabidopsis* genome project that span CIC1B8. These clones have insert lengths of approximately 70-100 kb and were used as probes on DNA blots with EcoRV-digested DNA from plants containing fast-neutron induced flc1 mutations. Two overlapping clones, designated K6M1 and MYB9, detected several deleted bands in flc1-2. Random 10 to 20 kb fragments of K6M1 and MYB9 resulting from partial digestion with Sau3A1 were used to create a library in the binary vector pPZP211 (Hajdukiewicz et al., 1994), and individual clones from this library were used to transform the FRI in Ler line. The library was constructed with DNA from the Col background, which contains a late-flowering allele of FLC1. Thus, FRI in Ler plants transformed with a construct containing the Col allele of FLC1 will be late flowering. One of the clones from this library, 211-31, produced $T_1$ plants that were very late-flowering. Over one third of the plants underwent senescence without flowering after 8 months of growth.

Sequencing revealed three putative genes in 211-31. To determine which gene represented FLC1, the three candidate genes were examined from two additional fast-neutron flc1 alleles, flc1-3 and flc1-4, and one EMS-generated allele, flc1-1. Both of the fast-neutron alleles showed polymorphisms in bands resulting from the MADS box transcription factor. Determination of the DNA sequence of flc1-1, flc1-3, and flc1-4 revealed that all contained lesions in the first exon of the MADS box transcription factor. flc1-3 contains a 104 bp deletion that removes the start codon and flc1-4 contains a 7 bp deletion that results in a frame shift after the first 20 amino acids. flc1-1 contains a single-base transition at the first exon/intron junction that changes the conserved GT donor site to AT and presumably disrupts splicing. FLC1 cDNA was isolated by RT-PCR from the Col background and the sequence is presented below in the sequence listing.

Example 3

Generation of Late-Flowering Transgenic *Arabidopsis*

To determine the utility of FLC1 in altering flowering time, transgenic *Arabidopsis* were created containing two different FLC1 constructs. The first construct, 211-31, was made from genomic DNA containing FLC1 and its native promoter. The second construct, pSM7, contained the genomic coding region of FLC1 under control of the constitutive 35S promoter from cauliflower mosaic virus (Odell, et al. *Nature* 313, 810-2 1985.).

211-31 was transformed into FRI in Ler by *Agrobacterium* mediated transformation (Bechtold, et al., C. R. Acad. Sci. Paris, 316:1194, 1993). Untransformed FRI in Ler flowers after forming approximately 14 primary rosette leaves(Lee, et al. *Plant Journal* 6, 903-909 1994.). FRI in Ler plants transformed with 211-31 showed a dramatic delay in flowering due to the synergistic interaction of FRI and FLC1 to delay flowering (Table 3). Greater than 90% of transformants formed 50 or more leaves before flowering and 38% never flowered, even when grown under far-red-enriched light—conditions that strongly promote flowering in *Arabidopsis*. Thus, FLC1 over-expression can prevent flowering altogether for the life of the plant. Due to the increased duration of the vegetative phase of development in plants transformed with 211-31, biomass was increased by 10 fold. This demonstrates that over-expression of an FLC gene is capable of turning an early flowering plant into a late flowering plant.

pSM7 was transformed into wild-type Ler by *Agrobacterium* mediated transformation (Bechtold, et al., C. R. Acad. Sci. Paris, 316:1194, 1993) to determine the effect of constitutive expression of FLC1 in a normally early-flowering line. The results are summarized in Table 5. Of the transgenic plants obtained 30% were not significantly later than the Ler parent, 35% showed a moderate delay in flowering time, and 35% were quite late flowering. Part of the variation in flowering time of the transgenic plants may be due to differences in expression levels stemming from their insertion at different locations in the genome. This demonstrates that even in the absence of FRI activity, FLC1 expression is sufficient to substantially delay flowering. Furthermore, the delay in flowering caused by constitutive FLC1 expression is insensitive to vernalization (vernalization is effective in promoting flowering in naturally-occurring late-flowering lines containing FRI and FLC1). Thus by replacing the native FLC promoter with a constitutive promoter, it becomes possible to create late flowering plants in which the characteristic of late flowering is insensitive to environmental cues. Again the delay in flowering was associated with a substantial increase in biomass.

TABLE 3

Flowering time of FRI containing plants transformed with FLC1.*

| Rosette leaf number at flowering | Percentage of transformed plants |
| --- | --- |
| 12-20 leaves | 8% |
| 20-40 leaves | 0% |
| 40-80 leaves | 54% |
| >80 leaves | 38% |

*Untransformed FRI in Ler, which lacks FLC1 function, flowers after forming 12-14 rosette leaves, while 92% of transformed plants into which one or more copies of FLC1 have been introduced form at least 3 times as many leaves before flowering. The number of leaves formed before flowering is measure of flowering time. Thus, the introduction of the FLC1 gene into this line consistently causes the modified plants to require at least 6 fold longer time to flower. In several lines, flowering never occurred.

TABLE 4

Increase in biomass of FRI containing plants transformed with FLC1.*

| Lines | Fresh weight |
| --- | --- |
| FRI in Ler | 1.5 g (.14) |
| FRI in Ler transformed with 211-31 | 15.5 g (2.1) |

*Upon transformation with FLC1 the fresh weight of plants was increased by 10 fold. Numbers in parentheses represent one standard deviation.

TABLE 5

Flowering time of Ler plants transformed with a constitutively expressed FLC1.*

| Rosette leaf number at flowering | Percentage of transformed plants |
| --- | --- |
| 7-10 leaves | 30% |
| 10-20 leaves | 35% |
| >20 leaves | 35% |

*Wild-type Ler flowers after forming 7-8 leaves. 70% of primary transformants show delayed flowering, with 35% forming more than twice the number of leaves before flowering. The number of leaves formed before flowering is measure of flowering time. Thus, the time to flowering in lines constitutively expressing FLC1 is delayed by up to 3 fold or more.

Example 4

Examination of FLC1 Homologs From *Brassica*

FLC activity regulates flowering time in species other than *Arabidopsis*. To investigate this possibility, FLC1 homologs were isolated from *Brassica rapa* mRNA by RT-PCR using primers designed to the *Arabidopsis* FLC1 sequence. The nucleotide sequences of the *B. rapa* homologs (BrFLC1A and BrFLC1B) are presented in the sequence listing below. The amino acid identity between FLC1 and BrFLC1A and BrFLC1B is shown in Table 6. Overexpression constructs were created by placing BrFLC1A and BrFLC1B under control of the constitutive 35S promoter. These constructs were transformed into an early-flowering strain of *Arabidopsis* and the flowering time of the T1 plants was determined. Many of the *Arabidopsis* plants containing the *Brassica* overexpression constructs were delayed in flowering, forming over three times as many leaves before flowering than the untransformed controls. Thus, like overexpression of FLC1 from *Arabidopsis*, the FLC1 homologs isolated from *B. rapa* are able to delay flowering in *Arabidopsis* when constitutively expressed.

TABLE 6

Amino acid identity between FLC1 and Brassica rapa FLC1 homologs.

| | Identity within MADS domain* | Identity outside MADS domain | Total identity |
| --- | --- | --- | --- |
| BrFLC1A | 88% | 81% | 83% |
| BrFLC1B | 93% | 81% | 85% |

*For this comparison, amino acids 1-60 are considered to be the MADS domain. Because of the high degree of conservation within the MADS domain between family members, similarity inside and outside of the MADS domain is presented.

Example 5

Identification of FLC1-Like Genes in *Arabidopsis*

Database searches using the FLC1 sequence identified two other MADS domain genes, FLC2 and FLC3, with significant homology to FLC1. These genes were previously identifed by the *Arabidopsis* genome sequencing effort, although their function was unknown, and they are here designated FLC2 and FLC3. cDNA clones were obtained for FLC2 and FLC3 by RT-PCR. The nucleotide sequences of FLC2 and FLC3 are presented in the sequence listing below. The amino acid identity between FLC1 and FLC2 and FLC3 is shown in Table 7.

TABLE 7

Amino acid identity between FLC1 and FLC2 and FLC3.

|  | Identity within MADS domain* | Identity outside MADS domain | Total identity |
|---|---|---|---|
| FLC2 | 83% | 50% | 60% |
| FLC3 | 83% | 50% | 60% |

*For this comparison, amino acids 1-60 are considered to be the MADS domain. Because of the high degree of conservation within the MADS domain between family members, similarity inside and outside of the MADS domain is presented.

Example 6

FLC2 Acts to Supress Flowering in *Arabidopsis*

Loss-of-function alleles were identified in FLC2 by PCR based screening of a T-DNA insertional mutagenized population using established techniques (Krysan, Young, Sussman, T-DNA as an insertion mutagen in *Arabidopsis*. *Plant Cell*, v. 11, p.2283-2290, 1999). Two alleles were found, flc2-1 and flc2-2. In the flc2-1 allele the T-DNA is inserted at position 4138 of the genomic sequence, and the allele flc2-2 the T-DNA is inserted at the position 442. The effect of these loss-of-function mutations on flowering time was investigated under long-day and short-day conditions. The results are shown in Table 8. Like FLC1, FLC2 has a role in delaying flowering in *Arabidopsis*. Under long and short days the flc2 mutants flower earlier than the corresponding wild type; thus the wild-type role of FLC2 is to delay flowering.

TABLE 8

Effect of flc2 loss-of-function mutations on flowering time.

| Lines | Range of rosette leaf number at flowering |
|---|---|
| Long days-Wild type | 8-9 |
| Long days-flc2-1 | 6-7 |
| Long days-flc2-2 | 6-7 |
| Short days-Wild type | 25-30 |
| Short days-flc2-1 | 7-9 |
| Short days-flc2-2 | 9-11 |

Example 7

Overexpression of FLC2 Delays Flowering in *Arabidopsis*

To assess the effect of FLC2 overexpression on flowering time, the genomic coding region of FLC2 was placed under control of the constitutive 35S promoter and transformed into *Arabidopsis thaliana* by standard techniques (Bechtold et al, C. R. *Acad. Sci. Paris*, 316, 1194, 1993). The results are shown in Table 9. Like FLC1, overexpression of FLC2 is sufficient to delay flowering. Many transformed plants formed two to three times the number of leaves before flowering.

TABLE 9

Effect of FLC2 overexpression on flowering time*.

| Rosette leaf number at flowering | Percentage of transformed plants |
|---|---|
| 12-16 leaves | 55% |
| 17-33 leaves | 45% |

*Untransformed wild type flowers with 8-9 leaves.

This experimental data, taken as a whole, established that the FLC family of genes act to delay the time of flowering in plants. The data demonstrated that there is more than one native FLC gene in many, if not most, plants. While the FLC genes interact with other flowering timing genes like the FRI genes, the FLC genes alone can be used to alter flowering time in plants. The FLC genes encode proteins that have a high degree of sequence identity both within and across plant species, and FLC genes from one species do work in other species. Thus a useful tool is provided to manipulate and help control the timing of plant flowering across a wide ranges of plant species.

The complete disclosures of all patents, patent applications, publications, and nucleic acid and protein database entries, including for example GenBank accession numbers and EMBL accession numbers, that are cited herein are hereby incorporated by reference as if individually incorporated. It is also understood that, given the limitations of the state of the art, occasional sequence errors or deletions may occur without affecting the usefulness of the data presented. Various modifications and alterations of this invention will become apparent to those skilled in the art without departing from the scope and spirit of this invention, and it should be understood that this invention is not to be unduly limited to the illustrative embodiments set forth herein.

We claim:

1. A transgenic plant comprising in its genome a transgene encoding a Flowering Locus C2 (FLC2) gene, the transgene coding for a polypeptide comprising SEQ ID NO:4, wherein expression of the transgene causes a delay in the onset of flowering in the transgenic plant compared to non-transgenic plants of the same species.

2. A seed of the transgenic plant of claim 1, wherein the seed comprises the transgene.

3. A seed for a transgenic plant, the seed comprising in its genome a transgene comprising a plant expressible promoter and an antisense coding region complementary to a protein coding region for a plant Flowering Locus C2 (FLC2) protein, the plant FLC2 protein (i) having a MADS box domain, (ii) being identical in amino acid sequence to SEQ ID NO: 4, outside of the region of the MADS box domain, wherein expression of said antisense coding region in the transgenic plant causes early flowering as compared to a non-transgenic plant of the same genetic background.

4. A plant grown from the seed of claim 3.

5. An isolated nucleotide sequence comprising a coding sequence for a FLC2 gene, wherein the coding sequence is defined by SEQ ID NO:3.

6. An isolated DNA sequence comprising a DNA sequence encoding the FLC2 protein, wherein the FLC2 protein is defined by SEQ ID NO:4.

7. A genetic construction comprising a plant expressible promoter operably connected to an isolated protein coding sequence for a protein of the Flowering Locus C2 (FLC2) gene, the plant FLC2 protein (i) having a MADS box domain, (ii) being identical in amino acid sequence to SEQ ID NO:4, and (iii) effective when expressed in transgenic plants to cause a delay in the onset of flowering in the transgenic plant as compared to a non-transgenic plant of the same genetic background.

8. A transgenic plant comprising a transgene encoding a member of the plant Flowering Locus C2 (FLC2) protein, the plant FLC2 protein (i) having a MADS box domain, (ii) being identical in amino acid sequence to SEQ ID NO:4, and (iii) effective when expressed in transgenic plants to cause a delay in the onset of flowering in the transgenic plant as compared to a non-transgenic plant of the same genetic background.

9. A method of producing a transgenic plant with altered flowering characteristics comprising: contacting a plant cell with a transgene comprising a plant expressible promoter and a protein coding sequence encoding a plant Flowering Locus C2 (FLC2) gene protein, the plant FLC2 protein (i) having a MADS box domain, (ii) being identical in amino acid sequence to SEQ ID NO:4, and (iii) effective when expressed in transgenic plants to cause a delay in the onset of flowering in the transgenic plant as compared to a non-transgenic plant of the same genetic background; identifying a plant cell carrying the inserted transgene; regenerating a transgenic plant from the plant cell, wherein the transgenic plant exhibits at least about 10% more leaves than a non-transgenic plant of the same genetic background without the transgene, wherein the number of leaves is determined when the transgenic plant and the non-transgenic plant are being grown under the same conditions.

* * * * *

SEQUENCE LISTING

```
<160> NUMBER OF SEQ ID NOS: 10

<210> SEQ ID NO 1
<211> LENGTH: 797
<212> TYPE: DNA
<213> ORGANISM: Arabidopsis thaliana
<220> FEATURE:
<221> NAME/KEY: CDS
<222> LOCATION: (1)..(588)

<400> SEQUENCE: 1
```

```
atg gga aga aaa aaa cta gaa atc aag cga att gag aac aaa agt agc        48
Met Gly Arg Lys Lys Leu Glu Ile Lys Arg Ile Glu Asn Lys Ser Ser
1               5                   10                  15 cga caa gtc acc ttc tcc aaa cgt cgc aac ggt ctc atc gag aaa gct        96
Arg Gln Val Thr Phe Ser Lys Arg Arg Asn Gly Leu Ile Glu Lys Ala
            20                  25                  30 cgt cag ctt tct gtt ctc tgt gac gca tcc gtc gct ctt ctc gtc gtc       144
Arg Gln Leu Ser Val Leu Cys Asp Ala Ser Val Ala Leu Leu Val Val
        35                  40                  45 tcc gcc tcc ggc aag ctc tac agc ttc tcc tcc ggc gat aac ctg gtc       192
Ser Ala Ser Gly Lys Leu Tyr Ser Phe Ser Ser Gly Asp Asn Leu Val
    50                  55                  60 aag atc ctt gat cga tat ggg aaa cag cat gct gat gat ctt aaa gcc       240
Lys Ile Leu Asp Arg Tyr Gly Lys Gln His Ala Asp Asp Leu Lys Ala
65                  70                  75                  80 ttg gat cat cag tca aaa gct ctg aac tat ggt tca cac tat gag cta       288
Leu Asp His Gln Ser Lys Ala Leu Asn Tyr Gly Ser His Tyr Glu Leu
                85                  90                  95 ctt gaa ctt gtg gat agc aag ctt gtg gga tca aat gtc aaa aat gtg       336
Leu Glu Leu Val Asp Ser Lys Leu Val Gly Ser Asn Val Lys Asn Val
            100                 105                 110 agt atc gat gct ctt gtt caa ctg gag gaa cac ctt gag act gcc ctc       384
Ser Ile Asp Ala Leu Val Gln Leu Glu Glu His Leu Glu Thr Ala Leu
        115                 120                 125 tcc gtg act aga gcc aag aag acc gaa ctc atg ttg aag ctt gtt gag       432
Ser Val Thr Arg Ala Lys Lys Thr Glu Leu Met Leu Lys Leu Val Glu
    130                 135                 140 aat ctt aaa gaa aag gag aaa atg ctg aaa gaa gag aac cag gtt ttg       480
Asn Leu Lys Glu Lys Glu Lys Met Leu Lys Glu Glu Asn Gln Val Leu
145                 150                 155                 160 gct agc cag atg gag aat aat cat cat gtg gga gca gaa gct gag atg       528
Ala Ser Gln Met Glu Asn Asn His His Val Gly Ala Glu Ala Glu Met
                165                 170                 175 gag atg tca cct gct gga caa atc tcc gac aat ctt ccg gtg act ctc       576
Glu Met Ser Pro Ala Gly Gln Ile Ser Asp Asn Leu Pro Val Thr Leu
            180                 185                 190 cca cta ctt aat tagccacctt aaatcggcgg ttgaaatcaa aatccaaaac           628
Pro Leu Leu Asn
            195 atatataatt atgaagaaaa aaaaaataag atatgtaatt attccgctga taagggcgag    688 cgtttgtata tcttaatact ctctctttgg ccaagagact ttgtgtgtga tacttaagta    748 gacggaacta agtcaatact atccgtttta agacaaaaaa aaaaaaaaa                797

<210> SEQ ID NO 2
<211> LENGTH: 196
<212> TYPE: PRT
<213> ORGANISM: Arabidopsis thaliana

<400> SEQUENCE: 2

Met Gly Arg Lys Lys Leu Glu Ile Lys Arg Ile Glu Asn Lys Ser Ser
1               5                   10                  15

Arg Gln Val Thr Phe Ser Lys Arg Arg Asn Gly Leu Ile Glu Lys Ala
            20                  25                  30

Arg Gln Leu Ser Val Leu Cys Asp Ala Ser Val Ala Leu Leu Val Val
        35                  40                  45

Ser Ala Ser Gly Lys Leu Tyr Ser Phe Ser Ser Gly Asp Asn Leu Val
    50                  55                  60
```

```
Lys Ile Leu Asp Arg Tyr Gly Lys Gln His Ala Asp Leu Lys Ala
 65                  70                  75                  80

Leu Asp His Gln Ser Lys Ala Leu Asn Tyr Gly Ser His Tyr Glu Leu
                 85                  90                  95

Leu Glu Leu Val Asp Ser Lys Leu Val Gly Ser Asn Val Lys Asn Val
            100                 105                 110

Ser Ile Asp Ala Leu Val Gln Leu Glu Glu His Leu Glu Thr Ala Leu
            115                 120                 125

Ser Val Thr Arg Ala Lys Lys Thr Glu Leu Met Leu Lys Leu Val Glu
        130                 135                 140

Asn Leu Lys Glu Lys Glu Lys Met Leu Lys Glu Asn Gln Val Leu
145                 150                 155                 160

Ala Ser Gln Met Glu Asn Asn His His Val Gly Ala Glu Ala Glu Met
                165                 170                 175

Glu Met Ser Pro Ala Gly Gln Ile Ser Asp Asn Leu Pro Val Thr Leu
            180                 185                 190

Pro Leu Leu Asn
        195

<210> SEQ ID NO 3
<211> LENGTH: 907
<212> TYPE: DNA
<213> ORGANISM: Arabidopsis thaliana
<220> FEATURE:
<221> NAME/KEY: CDS
<222> LOCATION: (1)..(519)

<400> SEQUENCE: 3 atg gga aga aga aaa atc gag atc aag cga atc gag aac aaa agc agt      48
Met Gly Arg Arg Lys Ile Glu Ile Lys Arg Ile Glu Asn Lys Ser Ser
  1               5                  10                  15 cga caa gtc act ttc tcc aaa cga cgc aat ggt ctc atc gac aaa gct      96
Arg Gln Val Thr Phe Ser Lys Arg Arg Asn Gly Leu Ile Asp Lys Ala
                 20                  25                  30 cga caa ctt tcg att ctc tgt gaa tcc tcc gtc gct gtt gtc gtc gta     144
Arg Gln Leu Ser Ile Leu Cys Glu Ser Ser Val Ala Val Val Val Val
             35                  40                  45 tct gcc tcc gga aaa ctc tat gac tct tcc tcc ggt gac gac att tcc     192
Ser Ala Ser Gly Lys Leu Tyr Asp Ser Ser Ser Gly Asp Asp Ile Ser
         50                  55                  60 aag atc att gat cgt tat gaa ata caa cat gct gat gaa ctt aga gcc     240
Lys Ile Ile Asp Arg Tyr Glu Ile Gln His Ala Asp Glu Leu Arg Ala
 65                  70                  75                  80 tta gat ctt gaa gaa aaa att cag aat tat ctt cca cac aag gag tta     288
Leu Asp Leu Glu Glu Lys Ile Gln Asn Tyr Leu Pro His Lys Glu Leu
                 85                  90                  95 cta gaa aca gtc caa agc aag ctt gaa gaa cca aat gtc gat aat gta     336
Leu Glu Thr Val Gln Ser Lys Leu Glu Glu Pro Asn Val Asp Asn Val
            100                 105                 110 agt gta gat tct cta att tct ctg gag gaa caa ctt gag act gct ctg     384
Ser Val Asp Ser Leu Ile Ser Leu Glu Glu Gln Leu Glu Thr Ala Leu
            115                 120                 125 tcc gta agt aga gct agg aag gca gaa ctg atg atg gag tat atc gag     432
Ser Val Ser Arg Ala Arg Lys Ala Glu Leu Met Met Glu Tyr Ile Glu
        130                 135                 140 tcc ctt aaa gaa aag gag aaa ttg ctg aga gaa gag aac cag gtt ctg     480
Ser Leu Lys Glu Lys Glu Lys Leu Leu Arg Glu Glu Asn Gln Val Leu
145                 150                 155                 160 gct agc cag ctg tca gag aag aaa ggt atg tct cac cga tgaaagatac     529
```

-continued

```
Ala Ser Gln Leu Ser Glu Lys Lys Gly Met Ser His Arg
            165                 170 tcaaaacccg atgggaaaga atacgttgct ggcaacagat gatgagagag gaatgtttcc      589
gggaagtagc tccggcaaca aaataccgga gactctcccg ctgctcaatt agccaccatc      649
atcaacggct gagttttcac cttaaactca agcctgatt cataattaag agaataaatt       709
tgtatattat aaaagctgt gtaatctcaa accttttatc ttcctctagt gtggaattta       769
aggtcaaaaa gaaaacgaga agtatggat cagtgttgta cctccttcgg agacaagatc       829
agagtttgtg tgtttgtgtc tgaatgtacg gattggattt ttaaagttgt gctttctttc     889
ttcaaaaaaa aaaaaaaa                                                    907
```

<210> SEQ ID NO 4
<211> LENGTH: 173
<212> TYPE: PRT
<213> ORGANISM: Arabidopsis thaliana

<400> SEQUENCE: 4

```
Met Gly Arg Arg Lys Ile Glu Ile Lys Arg Ile Glu Asn Lys Ser Ser
1               5                   10                  15

Arg Gln Val Thr Phe Ser Lys Arg Arg Asn Gly Leu Ile Asp Lys Ala
            20                  25                  30

Arg Gln Leu Ser Ile Leu Cys Glu Ser Ser Val Ala Val Val Val Val
        35                  40                  45

Ser Ala Ser Gly Lys Leu Tyr Asp Ser Ser Ser Gly Asp Asp Ile Ser
    50                  55                  60

Lys Ile Ile Asp Arg Tyr Glu Ile Gln His Ala Asp Glu Leu Arg Ala
65                  70                  75                  80

Leu Asp Leu Glu Glu Lys Ile Gln Asn Tyr Leu Pro His Lys Glu Leu
                85                  90                  95

Leu Glu Thr Val Gln Ser Lys Leu Glu Glu Pro Asn Val Asp Asn Val
            100                 105                 110

Ser Val Asp Ser Leu Ile Ser Leu Glu Glu Gln Leu Glu Thr Ala Leu
        115                 120                 125

Ser Val Ser Arg Ala Arg Lys Ala Glu Leu Met Met Glu Tyr Ile Glu
    130                 135                 140

Ser Leu Lys Glu Lys Glu Lys Leu Leu Arg Glu Glu Asn Gln Val Leu
145                 150                 155                 160

Ala Ser Gln Leu Ser Glu Lys Lys Gly Met Ser His Arg
                165                 170
```

<210> SEQ ID NO 5
<211> LENGTH: 769
<212> TYPE: DNA
<213> ORGANISM: Arabidopsis thaliana
<220> FEATURE:
<221> NAME/KEY: CDS
<222> LOCATION: (1)..(534)

<400> SEQUENCE: 5

```
atg ggt aga aaa aaa gtc gag atc aag cga atc gag aac aaa agt agt       48
Met Gly Arg Lys Lys Val Glu Ile Lys Arg Ile Glu Asn Lys Ser Ser
1               5                   10                  15 cga caa gtc act ttc tcc aaa cga cgc aat ggt ctc atc gag aaa gct       96
Arg Gln Val Thr Phe Ser Lys Arg Arg Asn Gly Leu Ile Glu Lys Ala
            20                  25                  30 cga caa ctt tca att ctc tgt gaa tct tcc atc gct gtt ctc gtc gtc      144
Arg Gln Leu Ser Ile Leu Cys Glu Ser Ser Ile Ala Val Leu Val Val
        35                  40                  45
```

```
                   35                  40                  45
tcc ggc tcc gga aaa ctc tac aag tct gcc tcc ggt gac aac atg tca      192
Ser Gly Ser Gly Lys Leu Tyr Lys Ser Ala Ser Gly Asp Asn Met Ser
 50                  55                  60 aag atc att gat cgt tac gaa ata cat cat gct gat gaa ctt gaa gcc      240
Lys Ile Ile Asp Arg Tyr Glu Ile His His Ala Asp Glu Leu Glu Ala
 65                  70                  75                  80 tta gat ctt gca gaa aaa act cgg aat tat ctg cca ctc aaa gag tta      288
Leu Asp Leu Ala Glu Lys Thr Arg Asn Tyr Leu Pro Leu Lys Glu Leu
                 85                  90                  95 cta gaa ata gtc caa agc aag ctt gaa gaa tca aat gtc gat aat gca      336
Leu Glu Ile Val Gln Ser Lys Leu Glu Glu Ser Asn Val Asp Asn Ala
            100                 105                 110 agt gtg gat act tta att tct ctg gag gaa cag ctc gag act gct ctg      384
Ser Val Asp Thr Leu Ile Ser Leu Glu Glu Gln Leu Glu Thr Ala Leu
        115                 120                 125 tca gta act aga gct agg aag aca gaa cta atg atg ggg gaa gtg aag      432
Ser Val Thr Arg Ala Arg Lys Thr Glu Leu Met Met Gly Glu Val Lys
    130                 135                 140 tcc ctt caa aaa acg gag aac ttg ctg aga gaa gag aac cag act ttg      480
Ser Leu Gln Lys Thr Glu Asn Leu Leu Arg Glu Glu Asn Gln Thr Leu
145                 150                 155                 160 gct agc cag gtg aca aaa aca tct ctt gaa gct aat tca tca gtt gat      528
Ala Ser Gln Val Thr Lys Thr Ser Leu Glu Ala Asn Ser Ser Val Asp
                165                 170                 175 aca caa taaaaataga aattcacctt gcgttaaaca tatatatata aaagttgaag       584
Thr Gln gactttgatt gatgttaggc attttttttg tgaaaccccc atatatctta aaatctatga    644
taaaagtcct ttcaaaattc aaatttcttg ttactattta gttgaatgat cagttttaat   704
taatgaaatt ttcccaaaaa aaaaaaaaaa aaaaaaaaaa aaaaaaaaaa aaaaaaaaa    764 aaaaa                                                                769

<210> SEQ ID NO 6
<211> LENGTH: 178
<212> TYPE: PRT
<213> ORGANISM: Arabidopsis thaliana

<400> SEQUENCE: 6

Met Gly Arg Lys Lys Val Glu Ile Lys Arg Ile Glu Asn Lys Ser Ser
 1               5                  10                  15

Arg Gln Val Thr Phe Ser Lys Arg Arg Asn Gly Leu Ile Glu Lys Ala
            20                  25                  30

Arg Gln Leu Ser Ile Leu Cys Glu Ser Ser Ile Ala Val Leu Val Val
        35                  40                  45

Ser Gly Ser Gly Lys Leu Tyr Lys Ser Ala Ser Gly Asp Asn Met Ser
 50                  55                  60

Lys Ile Ile Asp Arg Tyr Glu Ile His His Ala Asp Glu Leu Glu Ala
 65                  70                  75                  80

Leu Asp Leu Ala Glu Lys Thr Arg Asn Tyr Leu Pro Leu Lys Glu Leu
                 85                  90                  95

Leu Glu Ile Val Gln Ser Lys Leu Glu Glu Ser Asn Val Asp Asn Ala
            100                 105                 110

Ser Val Asp Thr Leu Ile Ser Leu Glu Glu Gln Leu Glu Thr Ala Leu
        115                 120                 125

Ser Val Thr Arg Ala Arg Lys Thr Glu Leu Met Met Gly Glu Val Lys
    130                 135                 140
```

```
Ser Leu Gln Lys Thr Glu Asn Leu Leu Arg Glu Glu Asn Gln Thr Leu
145                 150                 155                 160

Ala Ser Gln Val Thr Lys Thr Ser Leu Glu Ala Asn Ser Ser Val Asp
                165                 170                 175

Thr Gln

<210> SEQ ID NO 7
<211> LENGTH: 863
<212> TYPE: DNA
<213> ORGANISM: Brassica rapa
<220> FEATURE:
<221> NAME/KEY: CDS
<222> LOCATION: (1)..(588)
<220> FEATURE:
<221> NAME/KEY: unsure
<222> LOCATION: (839)
<223> OTHER INFORMATION: unsure

<400> SEQUENCE: 7 atg gga aga aaa aaa cta gaa atc aag cga atc gag aaa aac agt agc      48
Met Gly Arg Lys Lys Leu Glu Ile Lys Arg Ile Glu Lys Asn Ser Ser
1               5                   10                  15 aga caa gtc acc tcc tgc aaa cga cgc aac ggt ctc atc gag aaa gct      96
Arg Gln Val Thr Ser Cys Lys Arg Arg Asn Gly Leu Ile Glu Lys Ala
            20                  25                  30 cgt cag ctt tct gtt ctc tgc gag gca tct gtt ggg ctt ctc gtt gtc     144
Arg Gln Leu Ser Val Leu Cys Glu Ala Ser Val Gly Leu Leu Val Val
        35                  40                  45 tcc gcc tcc gac aaa ctc tac agc ttc tcc tcc ggg gat aga ctg gag     192
Ser Ala Ser Asp Lys Leu Tyr Ser Phe Ser Ser Gly Asp Arg Leu Glu
50                  55                  60 aag atc ctt gat cga tat ggg aaa aaa cat gct gat gat ctc aat gcc     240
Lys Ile Leu Asp Arg Tyr Gly Lys Lys His Ala Asp Asp Leu Asn Ala
65                  70                  75                  80 ctg gat ctt cag tca aaa tct ctg aac tat agt tca cac cat gag cta     288
Leu Asp Leu Gln Ser Lys Ser Leu Asn Tyr Ser Ser His His Glu Leu
            85                  90                  95 cta gaa ctt gtg gaa agc aag ctt gtg gaa tca att gat gat gta agc     336
Leu Glu Leu Val Glu Ser Lys Leu Val Glu Ser Ile Asp Asp Val Ser
        100                 105                 110 gtg gat tcc ctc gtt gag cta gaa gat cac ctt gag act gcc ctc tct     384
Val Asp Ser Leu Val Glu Leu Glu Asp His Leu Glu Thr Ala Leu Ser
    115                 120                 125 gta act aga gct cgg aag gca gaa cta atg tta aag ctt gtt gaa agt     432
Val Thr Arg Ala Arg Lys Ala Glu Leu Met Leu Lys Leu Val Glu Ser
130                 135                 140 ctc aaa gaa aag gag aat ctg ctg aaa gaa gag aac cag gtt ttg gct     480
Leu Lys Glu Lys Glu Asn Leu Leu Lys Glu Glu Asn Gln Val Leu Ala
145                 150                 155                 160 agt cag att gag gag aaa aat ctt gag gga gcc gaa gct gat aat ata     528
Ser Gln Ile Glu Glu Lys Asn Leu Glu Gly Ala Glu Ala Asp Asn Ile
            165                 170                 175 gag atg tca tct gga caa atc tcc gac atc aat ctt cct gta act ctc     576
Glu Met Ser Ser Gly Gln Ile Ser Asp Ile Asn Leu Pro Val Thr Leu
        180                 185                 190 ccg ctg ctt aat taaccacctt tactcggcgg ttaatcaaaa taagaaacat         628
Pro Leu Leu Asn
        195 ataatctaaa gataacctat gtaggtttta cttttcgcag cttaattaac caccttact    688 cggcggttaa tcgaaattaa aaacatataa ttaacaaata acctatgtca gtttaacccc   748
```

```
ctgataaaga tgcacgttgt gcatcttagt tctctctctg gctgaggggc tgtgtaataa    808
ctatgcttag attaaataaa aatatatatc natctaagac aaaaaaaaaa aaaaa         863
```

<210> SEQ ID NO 8
<211> LENGTH: 196
<212> TYPE: PRT
<213> ORGANISM: Brassica rapa

<400> SEQUENCE: 8

```
Met Gly Arg Lys Lys Leu Glu Ile Lys Arg Ile Glu Lys Asn Ser Ser
 1               5                  10                  15

Arg Gln Val Thr Ser Cys Lys Arg Arg Asn Gly Leu Ile Glu Lys Ala
            20                  25                  30

Arg Gln Leu Ser Val Leu Cys Glu Ala Ser Val Gly Leu Leu Val Val
        35                  40                  45

Ser Ala Ser Asp Lys Leu Tyr Ser Phe Ser Ser Gly Asp Arg Leu Glu
    50                  55                  60

Lys Ile Leu Asp Arg Tyr Gly Lys Lys His Ala Asp Asp Leu Asn Ala
65                  70                  75                  80

Leu Asp Leu Gln Ser Lys Ser Leu Asn Tyr Ser Ser His His Glu Leu
                85                  90                  95

Leu Glu Leu Val Glu Ser Lys Leu Val Glu Ser Ile Asp Asp Val Ser
            100                 105                 110

Val Asp Ser Leu Val Glu Leu Glu Asp His Leu Glu Thr Ala Leu Ser
        115                 120                 125

Val Thr Arg Ala Arg Lys Ala Glu Leu Met Leu Lys Leu Val Glu Ser
    130                 135                 140

Leu Lys Glu Lys Glu Asn Leu Leu Lys Glu Glu Asn Gln Val Leu Ala
145                 150                 155                 160

Ser Gln Ile Glu Glu Lys Asn Leu Glu Gly Ala Glu Ala Asp Asn Ile
                165                 170                 175

Glu Met Ser Ser Gly Gln Ile Ser Asp Ile Asn Leu Pro Val Thr Leu
            180                 185                 190

Pro Leu Leu Asn
        195
```

<210> SEQ ID NO 9
<211> LENGTH: 867
<212> TYPE: DNA
<213> ORGANISM: Brassica rapa
<220> FEATURE:
<221> NAME/KEY: CDS
<222> LOCATION: (1)..(588)

<400> SEQUENCE: 9

```
atg gga aga aaa aaa cta gaa atc aag cga att gag aac aaa agt agc     48
Met Gly Arg Lys Lys Leu Glu Ile Lys Arg Ile Glu Asn Lys Ser Ser
 1               5                  10                  15 cga caa gtc acc ttc tcc aaa cga cgc agc ggt ctc atc gag aaa gct     96
Arg Gln Val Thr Phe Ser Lys Arg Arg Ser Gly Leu Ile Glu Lys Ala
            20                  25                  30 cgt cag ctt tct gtt ctc tgc gag gca tct gtt ggg ctt ctc gtt gtc    144
Arg Gln Leu Ser Val Leu Cys Glu Ala Ser Val Gly Leu Leu Val Val
        35                  40                  45 tcc gcc tcc gac aaa ctc tac agc ttc tcc tcc ggg gat aga ctg gag    192
Ser Ala Ser Asp Lys Leu Tyr Ser Phe Ser Ser Gly Asp Arg Leu Glu
    50                  55                  60
```

```
aag atc ctt gat cga tat ggg aaa aaa cat gct gat gat ctc aat gcc        240
Lys Ile Leu Asp Arg Tyr Gly Lys Lys His Ala Asp Asp Leu Asn Ala
 65                  70                  75                  80 ctg gat ctt cag tca aaa tct ctg aac tat agt tca cac cat gag cta        288
Leu Asp Leu Gln Ser Lys Ser Leu Asn Tyr Ser Ser His His Glu Leu
                 85                  90                  95 cta gaa ctt gtg gaa agc aag ctt gtg gaa tca att gat gat gta agc        336
Leu Glu Leu Val Glu Ser Lys Leu Val Glu Ser Ile Asp Asp Val Ser
            100                 105                 110 gtg gat tcc ctc gtt gag cta gaa gat cac ctt gag act gcc ctc tct        384
Val Asp Ser Leu Val Glu Leu Glu Asp His Leu Glu Thr Ala Leu Ser
        115                 120                 125 gta act aga gct cgg aag gca gaa cta atg tta aag ctt gtt gaa agt        432
Val Thr Arg Ala Arg Lys Ala Glu Leu Met Leu Lys Leu Val Glu Ser
130                 135                 140 ctc aaa gaa aag gag aat ctg ctg aaa gaa gag aac cag gtt ttg gct        480
Leu Lys Glu Lys Glu Asn Leu Leu Lys Glu Glu Asn Gln Val Leu Ala
145                 150                 155                 160 agt cag att gag aag aaa aat ctt gag gga gcc gaa gct gat aat ata        528
Ser Gln Ile Glu Lys Lys Asn Leu Glu Gly Ala Glu Ala Asp Asn Ile
                165                 170                 175 gag atg tca tct gga caa atc tcc gac atc aat ctt cct gta act ctc        576
Glu Met Ser Ser Gly Gln Ile Ser Asp Ile Asn Leu Pro Val Thr Leu
            180                 185                 190 ccg ctg ctt aat taaccacctt tactcggcgg ttaatcaaaa taagaaacat            628
Pro Leu Leu Asn
            195 ataatctaaa gataacctat gtaggtttta cttttcgcag cttaattaac cacctttact     688 cggcggttaa tcgaaattaa aaacatataa ttaacaaata acctatgtca gtttaacccc     748 ctgataaaga tgcacgttgt acatcttagt tctctctctg gctgaggggc tgtgtaataa     808 ctatgcttag attaaataaa aatatatatc tatttaagac aaaaaaaaaa aaaaaaaa       867

<210> SEQ ID NO 10
<211> LENGTH: 196
<212> TYPE: PRT
<213> ORGANISM: Brassica rapa

<400> SEQUENCE: 10

Met Gly Arg Lys Lys Leu Glu Ile Lys Arg Ile Glu Asn Lys Ser Ser
 1               5                  10                  15

Arg Gln Val Thr Phe Ser Lys Arg Arg Ser Gly Leu Ile Glu Lys Ala
            20                  25                  30

Arg Gln Leu Ser Val Leu Cys Glu Ala Ser Val Gly Leu Leu Val Val
        35                  40                  45

Ser Ala Ser Asp Lys Leu Tyr Ser Phe Ser Ser Gly Asp Arg Leu Glu
    50                  55                  60

Lys Ile Leu Asp Arg Tyr Gly Lys Lys His Ala Asp Asp Leu Asn Ala
 65                  70                  75                  80

Leu Asp Leu Gln Ser Lys Ser Leu Asn Tyr Ser Ser His His Glu Leu
                 85                  90                  95

Leu Glu Leu Val Glu Ser Lys Leu Val Glu Ser Ile Asp Asp Val Ser
            100                 105                 110

Val Asp Ser Leu Val Glu Leu Glu Asp His Leu Glu Thr Ala Leu Ser
        115                 120                 125

Val Thr Arg Ala Arg Lys Ala Glu Leu Met Leu Lys Leu Val Glu Ser
    130                 135                 140
```

```
-continued

Leu Lys Glu Lys Glu Asn Leu Leu Lys Glu Glu Asn Gln Val Leu Ala
145                 150                 155                 160

Ser Gln Ile Glu Lys Lys Asn Leu Glu Gly Ala Glu Ala Asp Asn Ile
            165                 170                 175

Glu Met Ser Ser Gly Gln Ile Ser Asp Ile Asn Leu Pro Val Thr Leu
            180                 185                 190

Pro Leu Leu Asn
        195
```